United States Patent [19]

Kassman

[11] Patent Number: 4,961,734
[45] Date of Patent: Oct. 9, 1990

[54] CONDOM APPLICATOR AND PACKAGING

[76] Inventor: Leon B. Kassman, 208 W. 29th St., New York, N.Y. 10001

[21] Appl. No.: 206,182

[22] Filed: Jun. 10, 1988

[51] Int. Cl.⁵ .............................................. A61M 25/00
[52] U.S. Cl. .................................... 604/349; 128/844; 206/69
[58] Field of Search ........................ 128/844, 879, 880; 206/69; 604/346–353, 264

[56] References Cited

U.S. PATENT DOCUMENTS

| | | | |
|---|---|---|---|
| 1,687,717 | 10/1928 | Epstein | 604/349 |
| 4,540,409 | 9/1985 | Nystrom et al. | 604/349 |
| 4,589,875 | 5/1986 | Stringer | 604/351 |
| 4,805,604 | 2/1989 | Spery | 128/844 |

FOREIGN PATENT DOCUMENTS

| | | | |
|---|---|---|---|
| 0260025 | 3/1988 | European Pat. Off. | 604/349 |
| 0406507 | 11/1924 | Fed. Rep. of Germany | 604/349 |
| 8100174 | 2/1981 | PCT Int'l Appl. | 604/359 |
| 2120102 | 11/1983 | United Kingdom | 604/349 |
| 2191095 | 12/1987 | United Kingdom | 604/347 |
| 8701582 | 3/1987 | World Int. Prop. O. | 604/347 |
| 8802624 | 4/1988 | World Int. Prop. O. | 128/844 |

Primary Examiner—John D. Yasko
Assistant Examiner—Anthony M. Gutowski
Attorney, Agent, or Firm—Abelman, Frayne, Rezac & Schwab

[57] ABSTRACT

An applicator for a condom includes an axial wall of accordion pleated buttressed tooth form which is extendable from a collapsed condition to an extended position and will resist collapsing thereof towards the retracted position, and a condom is contained within the applicator in hermetically sealed relation therewith, such that the condom is expanded upon axial extension of the applicator.

4 Claims, 1 Drawing Sheet

CONDOM APPLICATOR AND PACKAGING

FIELD OF THE INVENTION

This invention relates to an applicator for a condom of any commonly known type and to the applicator of the invention when packaged in conjunction with a condom for sale as a pre-assembled unit.

BACKGROUND OF THE INVENTION

Condoms in a variety of forms are well-known in the art, and essentially are comprised of a thin tubular film of a readily expandable material, commonly latex or a plastisol, which has been formed with an impervious end enclosure, the tubular portion of the condom having been rolled to provide a relatively stable ring.

The application of the condom can be troublesome and time-consuming owing to the flexibility and compliance of the condom in its rolled form, and, the tendency of the condom to become unrolled before it is properly applied.

Collapsible and axially expandable tubes and bottles also are well known in the art for use as construction toys or for the storaqe of foods or chemicals. U.S. Pat. No. 3,908,704 teaches such expandable and collapsible tubular constructions.

SUMMARY OF THE INVENTION

It is an object of this invention to provide an applicator for use in conjunction with a conventional condom to facilitate application of the condom.

It is also an object of this invention to provide a combined condom and applicator assembly as a complete unit which can be pre-packaged for sale at a point of retail.

According to the present invention, the applicator is comprised of a collapsible and axially expandable tube of the type commonly known as a "popit" which has been formed with a hermetically closed end and an open end having a ring-shaped flange for the reception of a rolled portion of a condom.

As a direct extension of the concept of the present invention, a condom is positioned within the collapsed axially-expandable tube, and, the open end of the condom is detachably attached to the ring-shaped flange in a hermetically sealed manner with the major portion of the condom positioned in close proximity to the inner wall of the collapsed applicator.

Additionally, according to the present invention, a quantity of lubricant is contained within the applicator and fills or at least partially fills any existing air-spaces between the exterior surface of the condom and the interior surface of the applicator. The invention also contemplates the evacuation or partial evacuation of such air-spaces during the assembly of the condom onto the applicator.

It is contemplated that the applicator be made available for use with condoms of any manufacturer, or, in the alternative, that the applicator and condom be pre-assembled at the point of manufacture for sale as an assembled unit.

In order to ready the applicator for use, the applicator is expanded axially, and, by virtue of the axial expansion of the applicator, causes a negative pressure to be developed between the inner wall of the applicator and the outer surface of the condom, thus causing the condom to expand in unison with the applicator. The condom can then be applied, the hermetic seal between the free end of the condom and the ring-shaped flange of the applicator then being broken by manually rolling the free end of the condom axially off the ring-shaped flange of the applicator, thus freeing the applicator from the condom for disposal of the applicator. On release of the hermetic seal between the condom and the applicator the condom will contract under its own elastic memory, thus permitting the applicator to be withdrawn axially of the condom leaving the condom exposed, and in a pre-lubricated condition in the event that lubricant has been incorporated into the applicator.

DESCRIPTION OF THE PREFERRED EMBODIMENTS

Figures 1, 2:
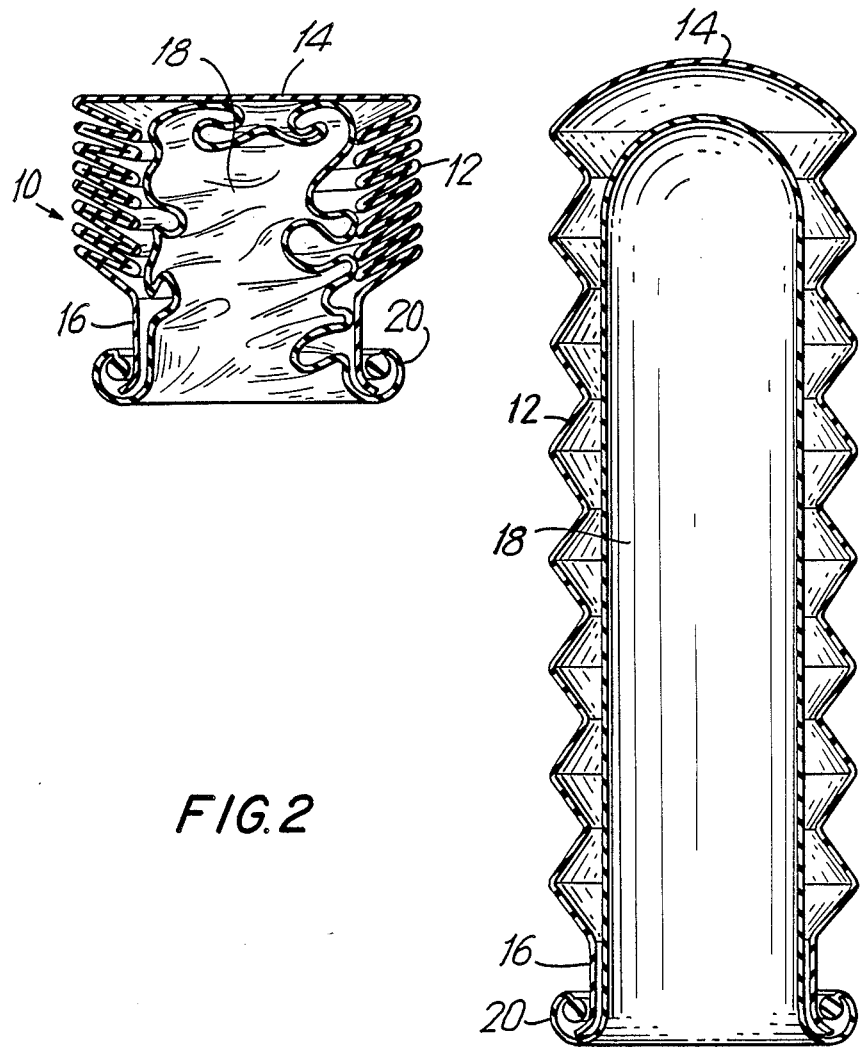
FIG. 1 is a cross-section of the applicator of the invention in an initial contracted or collapsed condition prior to the axial expansion thereof, and showing a conventional condom contained within the applicator.
FIG. 2 is a diagrammatic cross-section of the applicator when in an expanded condition and preparatory to its separation from the condom.

Referring to FIG. 1, the applicator of the present invention is indicated generally at 10 and is comprised of an axial impervious tubular wall 12 of buttressed tooth form as known in the art, having the form of a Chinese lantern, and an end closure wall 14 also formed from an impervious material and hermetically sealing that end of the wall 12. At its opposite axial end, the tubular wall 12 continues into an axially extending flange 16, which also is formed of an impervious material and hermetically sealed to the tubular wall 12.

Conveniently, the applicator can be formed from a suitable plastics material, such as polyvinyl chloride, or, it can be formed from a coated paper board material of sufficient strength to resist collapsing when the applicator is in its axially extended condition.

The axially extending tubular wall 12 of the applicator is formed in a manner known per-se for it to initially resist axial expansion, and, when expanded axially for it to resist axial contraction again in a manner known per-se.

In use of the applicator, preferably a quantity of a lubricant gel is inserted into the applicator, subsequent to which a partially unrolled condom is loosely stuffed into the applicator, and then, the remaining rolled free-end of the condom is stretched over the ring-shaped flange 16 in order to locate the condom within the axially compressed applicator.

In the alternative, the condom can be inserted into the applicator at the point of manufacture, in which event the assembly operation preferably is performed under negative pressure in order to evacuate air from the space between the outer surface of the condom and the inner surface of the applicator. Again, preferably a quantity of lubricant gel is inserted into the applicator prior to insertion of the condom.

In FIG. 1 of the drawings the condom 18 has been shown as pre-assembled into the applicator 10 in a condition readied for use.

In the event that the applicator is to be sold with the condom installed, the applicator and its contained condom will be packaged in a sterile manner. If the condom is the manufacture of some other manufacturer, then, it can be installed within the applicator in the manner discussed above.

Reference is now made to FIG. 2 which shows the applicator in an axially expanded condition and the condom readied for application.

As will be apparent, on axial expansion of the applicator 10, the internal volume of the applicator is very considerably increased and, by virtue of the hermetic seal between the outer surface of the condom 18 and the inner surface of the applicator 10, that portion of the condom which has been installed within the applicator is expanded outwardly and axially into substantial conformity with the inner wall of the applicator.

In the event that a lubricant gel has been inserted into the applicator prior to installation of the condom, the lubricant will act to insure free movement of the portion of the condom contained within the applicator thus resisting tearing or abrasion thereof and, in addition, will serve to reduce the amount of air present in the space between the outer surface of the condom and the inner surface of the applicator. As mentioned above, if the installation is to be made at the point of manufacture, it can be done under negative pressure in order to further reduce the volume of air contained within the space between the outer surface of the condom and the inner wall of the applicator.

The applicator itself is of the known form which will retain its position of axial extension such a construction being commonly known in storage jars or bottles, which can be expanded to any volume intermediate a maximum volume and a minimum volume, and which will retain its stability in any intermediate position of adjustment.

Preferably, the permissible axial extension of the applicator is such that it will produce outward balooning of the condom upon the application of an axial expansion force to the applicator, to facilitate application of the condom.

Once the hermetic seal provided by the rolled portion 20 of the condom has been broken by rolling it off the edge of the ring-shaped flange 16, air can enter the space between the exterior surface of the condom and the inner surface of the applicator, at which time the condom, if held in an inflated condition, will contract away from the wall 12 of the applicator and permit ready withdrawal of the applicator 10 axially of the condom 18.

Preferably a quantity of sterilized lubricant gel is contained within the applicator 10 to provide for prelubrication of the condom in addition to enhancing the vacuum force exerted on the condom during axial expansion of the applicator, and also to lubricate the condom during the axial expansion of the applicator and permit its ready sliding relative to the inner surface of the applicator thus eliminating the possibility of tearing or abrading the condom.

Also, preferably, the open spaces between the condom 18 and the inner wall of the collapsed applicator 10 are evacuated or partially evacuated during assembly of the device, again to increase the vacuum exerted on the condom 18 upon axial extension of the applicator 10.

By use of the invention, and subsequent to axial expansion of the applicator, a person is enabled to apply the condom using but a single hand, and then to release the condom from the applicator again by the use of a single hand, and with that hand then to dispose of the applicator.

Instead of assembling the condom into the applicator under negative pressure, as described above, the condom can be inserted into an axially expanded applicator and then be internally inflated to expand it into contact with the interior wall of the applicator prior to the rolled portion of the condom's being hermetically sealed onto the ring-shaped flange. Subsequent to assembly, the applicator can then be collapsed axially for packaging or storage.

As will be appreciated, the applicator can be made of larger diameter than that of a conventional condom, in that the applicator is capable, when axially expanded, of inflating the condom to considerably more than its initial diameter.

Also the axial length of the expanded applicator can be adjusted according to the preference of the user.

Upon release of the hermetic seal between the applicator and the condom, the condom has the capability of returning towards its initial size under the inherent elastic memory of the material from which it has been formed, again providing accommodation to the user of the device.

I claim:

1. In combination, a condom and an applicator therefore;

said applicator being comprised of a closed-ended tubular member having a accordion pleated axial wall of buttressed tooth form which is resistive to axial contraction subsequent to axial expansion thereof, and, a ring-shaped flange at the open end of said applicator;

said condom having a major portion including its closed axial-end contained within said applicator, and having the remaining portion of its length rolled and expanded over said ring-shaped flange to provide a hermetic seal therewith;

said major portion of said condom being positioned in at least close proximity with the interior of said collapsed applicator;

whereby, upon axial expansion of said applicator, said condom will be expanded outwardly and inflated into substantial conformity with the inner wall of said axially expanded applicator.

2. The combination of claim 1, including a quantity of lubricant gel contained within said applicator and at least partially filling air-spaces existing between the outer surface of said condom and the inner wall of said axially collapsed applicator.

3. The combination of claim 2 in which said air spaces have been intentionally at least partially evacuated during assembly of the condom into said axially collapsed applicator.

4. The combination of claim 1 in which said condom has been internally inflated into at least proximity with the interior wall of an axially expanded applicator, and hermetically sealed to the applicator prior to axial collapsing of the applicator.

* * * * *